US010953347B2

(12) United States Patent
Schab et al.

(10) Patent No.: US 10,953,347 B2
(45) Date of Patent: Mar. 23, 2021

(54) METHOD FOR PURIFYING GLYCOL USED AS A HYDRATE INHIBITOR

(71) Applicant: Novasep Process, Pompey (FR)

(72) Inventors: Frédéric Schab, Lyons (FR); Michel Cotillon, Vétheuil (FR); Teddy Ebran, Pont de Chéruy (FR); Vincent Gavroy, Lyons (FR)

(73) Assignee: Novasep Process, Pompey (FR)

( * ) Notice: Subject to any disclaimer, the term of this patent is extended or adjusted under 35 U.S.C. 154(b) by 569 days.

(21) Appl. No.: 15/326,812

(22) PCT Filed: Jul. 22, 2015

(86) PCT No.: PCT/EP2015/066765
§ 371 (c)(1),
(2) Date: Jul. 10, 2017

(87) PCT Pub. No.: WO2016/012500
PCT Pub. Date: Jan. 28, 2016

(65) Prior Publication Data
US 2017/0361247 A1    Dec. 21, 2017

(30) Foreign Application Priority Data
Jul. 25, 2014   (FR) ..................................... 14 57249

(51) Int. Cl.
*B01D 15/24*       (2006.01)
*C10L 3/10*        (2006.01)
*B01D 15/18*       (2006.01)
*C07C 29/76*       (2006.01)
*B01D 15/36*       (2006.01)
*C07C 41/36*       (2006.01)

(52) U.S. Cl.
CPC ....... *B01D 15/247* (2013.01); *B01D 15/1821* (2013.01); *B01D 15/362* (2013.01); *B01D 15/363* (2013.01); *B01D 15/365* (2013.01); *C07C 29/76* (2013.01); *C07C 41/36* (2013.01); *C10L 3/107* (2013.01); *C10L 2290/08* (2013.01); *C10L 2290/12* (2013.01); *C10L 2290/24* (2013.01); *C10L 2290/44* (2013.01); *C10L 2290/541* (2013.01); *C10L 2290/545* (2013.01)

(58) Field of Classification Search
CPC combination set(s) only.
See application file for complete search history.

(56) References Cited

U.S. PATENT DOCUMENTS

| 2,771,193 | A   |    | 11/1956 | Simpson et al. |
| 5,817,889 | A   |    | 10/1998 | Pondebat et al. |
| 9,174,902 | B2  | *  | 11/2015 | Soper ...................... C07C 29/74 |
| 9,433,875 | B2  |    | 9/2016  | Phelps et al. |
| 2010/0099807 | A1 | * | 4/2010 | Carlise .................... C10L 3/003 524/377 |
| 2012/0145645 | A1 | * | 6/2012 | Wietholter ............ C02F 1/5236 210/723 |
| 2014/0054160 | A1 | * | 2/2014 | Phelps ................... B01D 15/36 203/18 |

FOREIGN PATENT DOCUMENTS

| WO |     1995011876 A1 | 5/1995 |
| WO | WO 2014/031269 A1 | 2/2014 |
| WO | WO 2014/035740 A1 | 3/2014 |
| WO |     2014193889 A1 | 12/2014 |

OTHER PUBLICATIONS

Igunnu et al. ("Produced water treatment technologies"; Int J Low-Carbon Tech; 2014; 9; p. 157-177). (Year: 2014).*

Thompson et al. "Characterization of Crude Glycerol From Biodiesel Production From Multiple Feedstocks". (Applied Engineering in Agriculture, vol. 22(2), 2006, p. 261-265). (Year: 2006).*

International Search Report for PCT/EP2015/066765, entitled "Method for Purifying Glycol Used as a Hydrate Inhibitor," dated Jan. 10, 2015.

* cited by examiner

*Primary Examiner* — Ryan B Huang
(74) *Attorney, Agent, or Firm* — Hamilton, Brook, Smith & Reynolds, P.C.

(57) ABSTRACT

The invention concerns a purification method comprising:
  providing a flow comprising a glycol, monovalent ions and multivalent ions;
  treating this flow with ion exclusion chromatography comprising:
    injecting the flow into a chromatographic unit comprising an ion exchange stationary phase;
    injecting an eluent into the chromatographic unit;
    collecting a fraction at the outlet of the chromatographic unit;
  the collected fraction being enriched with glycol and depleted of monovalent ions and multivalent ions relative to the flow.

The invention also concerns an installation adapted to implement this method, and its application to the regeneration of an anti-hydrate agent.

11 Claims, 3 Drawing Sheets

METHOD FOR PURIFYING GLYCOL USED AS A HYDRATE INHIBITOR

This application is the U.S. National Stage of International Application No. PCT/EP2015/066765, filed Jul. 22, 2015, which designates the U.S., published in French, and claims priority under 35 U.S.C. § 119 or 365 to France Application No. FR1457249, filed Jul. 25, 2014. The entire teachings of the above applications are incorporated herein by reference.

FIELD OF THE INVENTION

The present invention relates to a glycol purification method, in particular within the context of the regeneration of an anti-hydrate agent used for conveying hydrocarbons.

TECHNICAL BACKGROUND

The extraction of hydrocarbons from undersea deposits is achieved by recovering a multiphase mixture formed of gaseous hydrocarbons (in particular natural gas) and/or liquid hydrocarbons and deposit seawater.

Under certain low temperature and high pressure conditions prevailing at the seafloor, natural gas may form a crystalline solid with water via Van der Waals-type bonds, known as gas hydrate or simply hydrate.

Hydrates may obstruct hydrocarbon lines which can cause complete stoppage of production and damage surface equipment such as valves and measuring instruments.

To prevent the formation of hydrates, it is known to use anti-hydrate agents, also known as hydrate inhibitors, and more particularly glycols such as monoethylene glycol (MEG, the most frequently used) or diethylene glycol (DEG) or triethylene glycol (TEG). Glycol is generally injected in concentrated form into the extracted multiphase mixture at the extraction well. It then dilutes in the aqueous phase of the multiphase mixture and mixes with impurities such as sea mineral salts or rock. The main ions contained in the multiphase mixture are sodium, potassium, magnesium, calcium, chloride, sulfate and carbonate ions.

The multiphase mixture, comprising the gaseous and/or liquid hydrocarbons and water containing salts and glycol, generally transits via a tank positioned on the seafloor before rising to the surface under the effect of pressure via piping for treatment on a platform.

After separating the gaseous and liquid hydrocarbons, the water containing salts and glycol (also known as "rich glycol") must be treated before the glycol can be recovered and recycled.

One known treatment technique is first to concentrate the solution by evaporation of the water followed by distilling the glycol, these operations possibly being carried out in one same distillation column. The salts crystallize and deposit at the bottom of the distillation column before being evacuated towards a centrifuging unit where the distillation residue is separated from the crystals at the bottom of the column. In this manner, a flow of purified, concentrated glycol is obtained (also known as "lean glycol"), which can be recycled. This technique has several disadvantages.

Distillation of the entirety of the glycol flow leads to very high energy consumption and operating costs.

The salts of divalent ions such as calcium or magnesium carbonate or sulfate have low solubility in an aqueous phase and form a precipitate on the walls of piping and heat exchangers, thereby reducing their exchange capacity and hence increasing energy consumption. Fouling of the installations may also require frequent cleaning. Therefore, the concentrations of divalent ions in rich glycol must be controlled, in particular when regeneration thereof involves temperatures possibly reaching 150° C., since the solubility of the divalent salts decreases when temperature increases.

Document CA 2838617 discloses a method for the pre-treatment of rich glycol by heating, to degas and precipitate the divalent cations associated with carbonates before regeneration.

Document WO 2009/017971 offers a method for the chemical precipitation of divalent cations through the addition of $Na_2CO_3$ and control of alkaline pH with sodium hydroxide, forming $CaCO_3$ and $MgCO_3$. The growth of $CaCO_3$ crystals is a slow method requiring long residence times.

Document GB 2473213 offers a similar method wherein temperature and alkaline pH conditions are maintained, allowing crystal growth. In addition, it offers injecting an inert gas at the bottom of the tank to remove impurities by flotation: the impurities adsorb on the surface of gas bubbles to create a foam that is removed from the surface of the glycol.

Document US 2010/0191023 offers adding $CaCO_3$ crystals to rich glycol to accelerate the crystal growth rate. The crystals are then decanted and the supernatant is filtered, providing lean glycol with a residual $CaCO_3$ content of less than 10 ppm.

All the methods using precipitation of the divalent salts described above are performed on rich glycol before evaporation of water and have several disadvantages. First, they require a long contact time related to crystallization, and hence large-volume crystallization tanks. Second, they require the use of chemical products such as $Na_2CO_3$ and NaOH which later have to be removed at the distillation step with the monovalent salts that are not removed by the precipitation step.

Separation of the glycol from the salt crystals can be obtained using several different techniques. Document FR 2846323 describes the use of filtration, centrifugation or ultrasound separation.

The separation and evacuation of the crystallized salts after glycol distillation is a difficult step to carry out, with high risks of fouling filters and blocking pipelines. With regard to centrifugal separation, the rotating equipment used requires regular maintenance operations.

To overcome these difficulties related to the presence of crystals, document US 2005/0022665 offers glycol/salt purification by nanofiltration of rich glycol before water evaporation, the membrane retaining part of the glycols and allowing part of the salts in solution to pass into the permeate. However, first this technique only allows partial demineralization of rich glycol with an insufficient recovery rate. Second, it is a costly technique which requires a membrane surface area proportional to the treated flow and relatively high energy consumption related to the osmotic pressure of the rich glycol.

Similarly, document U.S. Pat. No. 5,505,855 discloses the purification of non-aqueous TEG having high viscosity by reverse osmosis, the TEG being retained by the membrane which allows the salts to pass.

Document FR 2711650 teaches the use of an electrodialysis method. The rich glycol is first filtered to remove the matter in suspension. The filtrate is treated by electrodialysis whereby the glycol is demineralized by selective passing of the anions and cations through membranes solely permeable to the former or the latter, owing to the action of an electrical current and electrodes arranged on either side of the stack of membranes. This document also teaches the use of ion exchange resins for selective fixing of the anions or cations.

However, electrodialysis has the disadvantage of not removing salts in sufficient proportion, which means that in practice it must be completed by a so-called finishing step capable of removing the residual salts; in addition, it yields a glycol recovery rate that is lower than 97%. Additionally, the use of the ion exchange technique has the disadvantage of necessitating frequent, costly regeneration of the resin. This regeneration entails the use of large amounts of acid and base. Also, the total volume of adsorbent used and the total volume of chemical products used for such regeneration are directly proportional to the quantity of salts to be removed and hence to the load of the rich glycol to be treated. A further disadvantage relates to the large volumes of acid and base effluent to be treated and eliminated.

Document FR 2899822 is another example of a technique to demineralize an anti-hydrate agent via ion exchange on a substrate.

Outside the area of the regeneration of anti-hydrate agents, document WO 94/26684 claims a method for the purification and recovery of a mixture of DEG and terephthalate oligomers for the production of polyethylene terephthalate, the mixture containing metal oxides used as catalysts, coloring agents and other impurities to be removed. The mixture is heated to allow solubilization of the oligomers in the DEG, and it is then subjected to the following steps: filtering though activated charcoal, passing over a cationic resin, passing over an anionic resin, mixed bed and distillation. The use of an ion exchange step entails the above-mentioned disadvantages.

Document GB 2091580 discloses a chromatographic separation to purify and recycle the ethylene glycol contained in washing waters derived from the production of ethylene oxide. Document WO 2014/035740 concerns a method to reduce contaminants in a glycolic product obtained by hydrogenolysis of saccharides from biological or renewable sources, using ion exclusion chromatography followed by distillation.

In both documents, the objective of chromatographic purification is to separate the glycol from organic acids which form salts with the sodium ion.

Document U.S. Pat. No. 2,771,193 in fact already disclosed the use of the ion exclusion chromatography technique to separate glycol from sodium chloride.

Neither of these two documents suggests the possible use of this technique to separate glycol from a complex ion mixture.

There is therefore still a need to simplify and improve methods for regenerating glycol-based anti-hydrate agents, and in particular a need to provide efficient, economical solutions to replace distillation of the rich glycol flow and salt crystallization.

There is therefore a need for a method to regenerate anti-hydrate agents that is robust, reliable, productive, having low energy consumption, consuming few or no chemical products and generating minimum effluent that is easy to recycle.

SUMMARY OF THE INVENTION

The invention is first directed towards a purification method comprising:
providing a flow comprising a glycol, monovalent ions and multivalent ions;
treating this flow by ion exclusion chromatography, comprising:

injecting the flow into a chromatographic unit comprising an ion exchange stationary phase;
injecting an eluent into the chromatographic unit;
collecting a fraction at the outlet of the chromatographic unit;
the collected fraction being enriched with glycol and depleted of monovalent ions and multivalent ions relative to the flow.

According to one embodiment, the method comprises a subsequent step of concentrating the collected fraction.

According to one embodiment, the glycol is selected from monoethylene glycol, diethylene glycol, triethylene glycol and mixtures thereof.

According to one embodiment, the monovalent ions comprise monovalent cations, and the multivalent ions comprise divalent cations; and preferably the monovalent cations comprise $Na^+$ and/or $K^+$ cations, and the divalent cations comprise $Ca^{2+}$ and/or $Mg^{2+}$ cations.

According to one embodiment the flow has a ratio, in equivalents, of divalent cations to total cations of 5 to 90%, preferably 8 to 75% and more preferably 10 to 50%.

According to one embodiment, the chromatographic unit is a multi-column unit with non-static bed, and preferably a chromatographic unit with simulated moving bed or actual moving bed, or with improved simulated moving bed, or with sequential simulated moving bed, and most preferably with sequential simulated moving bed.

According to one embodiment the eluent is water, preferably demineralized water or water derived from the step of concentrating the collected fraction.

According to one embodiment the treatment of the flow by ion exclusion chromatography is conducted at a temperature of 10 to 160° C., preferably 40 to 100° C., and more particularly 55 to 90° C.

According to one embodiment, the stationary phase is a cationic resin partly in monovalent cationic form and partly in divalent cationic form, the monovalent cationic form and the divalent cationic form preferably corresponding to ions contained in the flow.

According to one embodiment, in the collected fraction at least 50 mol. %, preferably at least 80 mol. %, more preferably at least 85 mol. %, further preferably at least 90 mol. % and still further preferably at least 95 mol. % of the monovalent ions and multivalent ions contained in the flow are removed.

According to one embodiment, at least 20 kg of glycol, preferably at least 40 kg of glycol, more preferably at least 90 kg of glycol per litre of stationary phase passes through the chromatographic unit before the stationary phase is subjected to washing; and ideally the stationary phase does not undergo any washing.

The invention also concerns a method to regenerate an anti-hydrate agent, comprising:
providing a multiphase mixture comprising hydrocarbons, a glycol and dissolved salts;
separating the hydrocarbons from this mixture, so as to recover an aqueous phase;
applying the purification method such as described above to the aqueous phase as a flow, and recovering a regenerated composition of anti-hydrate agent in the form of the collected, optionally concentrated, fraction.

According to one embodiment, the method comprises a step of clarifying the aqueous phase before applying the purification method, preferably by filtration, and/or a step of concentrating the aqueous phase.

The invention also concerns a purification installation comprising:

a feed line for a flow comprising a glycol, monovalent ions and multivalent ions;

an eluent feed line;

a chromatographic unit comprising an ion exchange stationary phase supplied by the flow feed line and eluent feed line and configured to perform ion exclusion chromatography;

a collecting line for a fraction enriched with glycol and depleted of monovalent ions and multivalent ions relative to the flow, connected to the outlet of the chromatographic unit.

According to one embodiment, the collecting line for the fraction enriched with glycol and depleted of monovalent ions and multivalent ions feeds a unit for concentrating the fraction enriched with glycol and depleted of monovalent ions and multivalent ions.

According to one embodiment, the glycol is selected from monoethylene glycol, diethylene glycol, triethylene glycol and combinations thereof.

According to one embodiment, the monovalent ions comprise monovalent cations, and the multivalent ions comprise divalent cations; and preferably the monovalent cations comprise $Na^+$ and/or $K^+$ cations, and the divalent cations comprise $Ca^{2+}$ and/or $Mg^{2+}$ cations.

According to one embodiment, the flow has a ratio, in equivalents, divalent cations to total cations of de 5 to 90%, or 8 to 75%, or 10 to 50%.

According to one embodiment, the chromatographic unit is a multi-column unit with non-static bed, and preferably a chromatographic unit with simulated moving bed, or with actual moving bed, or with improved simulated moving bed, or with sequential simulated moving bed, and more particularly with sequential simulated moving bed.

According to one embodiment, the eluent is water, preferably demineralized water; and particularly preferred is a water recycling line provided between the unit for concentrating the fraction enriched with glycol and depleted of monovalent ions and multivalent ions, and the eluent feed line.

According to one embodiment, the installation is provided with temperature regulating means configured so that the chromatographic unit operates at a temperature of 10 to 160° C., preferably 40 to 100° C., and more preferably 55 to 90° C.

According to one embodiment, the stationary phase is a cationic resin partly in monovalent cationic form and partly in divalent cationic form, the monovalent cationic form and the divalent cationic form corresponding to the ions contained in the flow.

The invention also concerns an installation to regenerate an anti-hydrate agent, comprising:

A feed line for a multiphase mixture comprising hydrocarbons, a glycol and dissolved salts;

a hydrocarbon separation unit supplied by this multiphase mixture feed line;

a draw-off line for an aqueous phase derived from the hydrocarbon separation unit;

the above-described purification installation, in which the flow feed line is supplied by the aqueous phase draw-off line;

a collecting line for a regenerated composition of anti-hydrate agent, supplied by the collecting line for the fraction enriched with glycol and depleted of monovalent ions and multivalent ions, or optionally by a collecting line from the unit for concentrating the fraction enriched with glycol and depleted of monovalent ions and multivalent ions.

According to one embodiment, this installation comprises a unit for clarification of the aqueous phase, preferably a filtration unit and/or a unit to concentrate the aqueous phase, upstream of the purification installation.

With the present invention, it is possible to overcome the disadvantages of the prior art. In particular, it provides a glycol purification method that can particularly be applied in a method to regenerate an anti-hydrate agent containing glycol. This method is simplified and improved, more efficient and more economical than the prior art methods. The method of the invention is robust, reliable, productive, consumes little energy, consumes few or no chemical products, and generates minimum effluent that is easy to recycle.

This method is based on a chromatographic separation step which requires little or no washing or conditioning of the stationary phase.

This is achieved through the discovery that the ion exclusion chromatography technique allows very efficient separation of glycol both from monovalent ions and from multivalent ions (divalent ions in particular) that are generally contained in the multiphase mixture that is collected when extracting hydrocarbons. This separation is conducted in a single chromatography step (i.e. a single stationary phase is used, distributed over one or more columns, and a single eluent).

Having regard to the different affinity of ion exchange resins for monovalent ions and multivalent ions, it could be expected to obtain poor separation performance due to the expected occurrence of different ionic forms depending on the resin regions and ion displacement fronts. In addition, multivalent ions (such as $Ca^{2+}$ ions in particular) are generally of larger size than monovalent ions ($Na^+$, $H^+$. . . ), which means that their presence reduces the inner volume of the stationary phase, this likely to have a negative impact on the quality of separation. This is the case when observing the purification of sugars for example.

Yet it has surprisingly been found that excellent separation of the glycol from the dissolved salts is obtained in a manner that is stable over time. The onset of precipitation phenomena could also be expected, in particular in the presence of calcium ions. However, it was surprisingly observed that this is not the case and again excellent separation of the glycol and salts is obtained in a manner that is stable over time.

DESCRIPTION OF EMBODIMENTS OF THE INVENTION

A more detailed, non-limiting description of the invention is given below.

The invention concerns the separation of glycol in an aqueous solution from salts dissolved in the form of monovalent and multivalent ions. In the following, the invention is more particularly described in an application of this principle for the regeneration of an anti-hydrate agent.

By "anti-hydrate agent" is meant a product able to inhibit, avert, prevent or reduce the formation of gas hydrates in multiphase mixtures comprising water and liquid and/or gaseous hydrocarbons.

In the invention, the anti-hydrate agent is a composition comprising a glycol. The glycol may be MEG, DEG or TEG but not limited thereto. It is also possible to use a combination of several of these compounds.

By "regeneration" is meant purifying the anti-hydrate agent of undesirable contaminants and of mineral salts in particular.

The anti-hydrate agent is used is first collected in the form of a multiphase mixture which, in general, is a mixture of gaseous and/or liquid hydrocarbons such as a mixture of hydrocarbons derived from a deposit, mixed in particular with water, the anti-hydrate agent (glycol) and contaminants such as mineral salts.

First an aqueous phase (containing glycol) is separated from a gaseous phase and oil phase. To this end, the mixture can be passed through a first separation column or expansion compartment for example, to separate the gaseous phase from the liquid phases. The liquid phases are then passed through a second compartment where the oil phase and aqueous phase are separated according to density, for example by decanting.

The gas and the liquid hydrocarbons are evacuated and stored in tanks. The aqueous phase then undergoes the following treatments provided by the invention.

Figure 1:
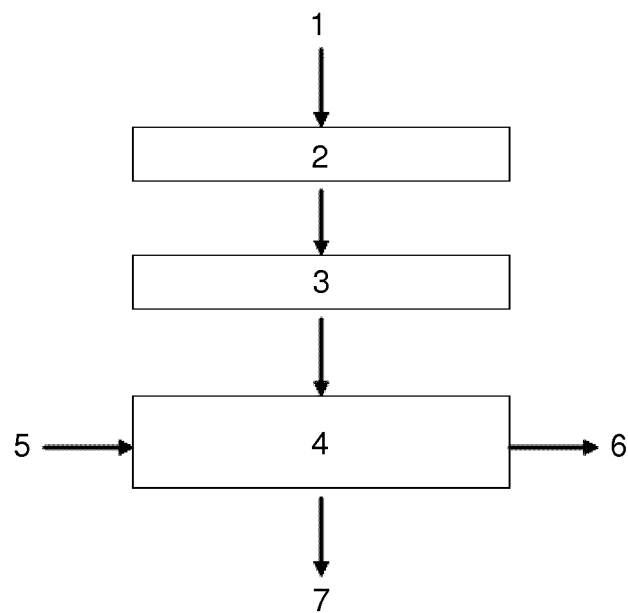
FIG. 1 is a block diagram illustrating the principle of the invention according to one particular embodiment.

With reference to FIG. 1, according to one embodiment of the invention, the aqueous phase 1 may first be subjected to an adjustment of temperature 2 using a heat exchanger—so that the temperature of the aqueous phase is adapted to the parameters of subsequent chromatographic separation. In general, this is a heating step (but cooling may be appropriate in some cases).

Next, the aqueous phase can undergo a clarification step 3 (in a clarification unit). This step can also be provided before the temperature adjustment step. Each of these two steps is optional. It is therefore possible to conduct only temperature adjustment, or only clarification, or temperature adjustment followed by clarification as illustrated, or clarification followed by temperature adjustment.

The clarification step 3 consists in reducing or eliminating matter in suspension. For this purpose, for example filtering can be used using a pocket or coil filter, basket filter or press filter, centrifugation, earth filtration with or without pre-coat and/or body feed, dead-end filtration, or crossflow filtration on a microfiltration or ultrafiltration-type membrane, or filtration on diatoms or ceramic membrane.

Then, the chromatography step 4 is implemented, which forms the core of the invention. In the following, the term "inflow" is used to designate the aqueous flow subjected to the chromatographic step 4.

At the outlet of this chromatography step 4, a fraction 6 that is enriched with glycol and depleted of ions, and a fraction 7 enriched with ions and depleted of glycol are collected. The chromatography step 4 is performed using also a flow of eluent 5 (e.g. a flow of demineralized water).

By "fraction enriched with glycol and depleted of ions" is meant a fraction in which the molar concentration ratio of glycol/total ions is higher than the ratio of the chromatography inflow (independently of the effects of concentration or global dilution with respect to water). Preferably, this ratio is higher by a factor of at least 2, or at least 3, or at least 5, or at least 8, or at least 10. This fraction is also called the "extract".

In general, said fraction enriched with glycol has a lower glycol concentration than the inflow. The dilution rate (ratio of glycol concentration in g/L in the fraction enriched with glycol to the glycol concentration in g/L in the inflow) can preferably be 0.4 to 1.00, in particular 0.60 to 0.99, and more particularly 0.65 to 0.95.

The fraction enriched with glycol (and depleted of ions) can undergo an optional concentration step (to reduce the water content and hence increase the glycol content), e.g. in an evaporator. This subsequent concentration step is particularly suitable for flows with high salt content, for which it is important to perform demineralization before passing through an evaporator. Alternatively, a concentration step can be provided before the chromatography step 4, which can make it possible to reduce the size of the chromatographic unit (described in more detail below). It is also possible to provide for concentration before and after the chromatography step 4. In this case, the two concentration steps can be carried out on one same item of equipment. In this case, it is possible to arrange the chromatographic unit on an evaporator recirculation line.

By "fraction enriched with ions and depleted of glycol", on the contrary is meant a fraction in which the molar concentration ratio of glycol/total ion is lower than the ratio in the chromatography inflow (independently of the effects of concentration or global dilution with respect to water). Preferably, this ratio is lower by a factor of at least 2, or at least 3, or at least 5, or at least 8 or at least 10. This fraction is also called the "raffinate".

The inflow treated by chromatography is an aqueous solution of glycol also containing monovalent ions and multivalent ions, especially divalent ions in solution. The composition of this flow is highly dependent on the source of the collected multiphase mixture. In particular, the type and content of the ions in solution is dependent upon the location and geological age of the well and on the type of rock in the deposit.

However, the invention is robust and makes it possible to adapt to various concentrations and efficiently treat them.

The glycol content of the inflow may vary from 1 to 1283 g/L and in particular from 200 to 900 g/L.

The total salt concentration in the inflow may range from 0.1 g/L up to the limit solubility concentration of the different species contained in the solution.

According to one embodiment, the inflow contains $Na^+$ and/or $K^+$ cations on the one hand; and $Ca^{2+}$ and/or $Mg^{2+}$ cations on the other hand.

According to one embodiment, the inflow contains $Na^+$, $K^+$, $Ca^{2+}$ and $Mg^{2+}$ cations.

It may also contain anions such as $Cl^-$, $SO_4^{2-}$ and $CO_3^{2-}$, and more particularly $Cl^-$ anions, these being the most soluble ones.

It is to be noted that numerous other metal ions in solution may be present such as $Fe^{2+}$, $Fe^{3+}$, $Cu^{2+}$, $Zn^{2+}$ ions etc. even if anti-corrosion agents are used.

More particularly, the inflow preferably contains 0.01 to 154 g/L of $Na^+$ ions, more particularly 0.1 to 100 g/L, further preferably 0.5 to 80 g/L, still further preferably 1 to 40 g/L and most preferably 2 to 15 g/L.

More particularly, the inflow preferably contains 0.01 to 178 g/L of $K^+$ ions, more preferably 0.1 to 100 g/L, further preferably 0.2 to 50 g/L, still further preferably 0.3 to 10 g/L and most preferably 0.5 to 4 g/L.

More particularly, the inflow preferably contains 0.01 to 268 g/L of $Ca^{2+}$ ions, more preferably 0.1 to 200 g/L, further preferably 0.2 to 100 g/L, still further preferably 0.5 to 50 g/L and most preferably 1 to 10 g/L.

More particularly, the inflow preferably contains 0.01 to 137 g/L of $Mg^{2+}$ ions, more preferably 0.02 to 80 g/L, further preferably 1 to 30 g/L, still further preferably 0.05 to 10 g/L and most preferably 0.1 to 1 g/L.

The ratio of divalent cations to total cations, in equivalents, is defined as the ratio of the total molar concentrations of the species concerned weighted by charge. For example, one mole of $Ca^{2+}$ ions is equivalent to two moles of $Na^+$ ions.

According to some embodiments, this ratio is from 5 to 10%; or from 10 to 15%; or from 15 to 20%; or from 20 to 25%; or from 25 to 30%; or from 30 to 35%; or from 35 to 40%; or from 40 to 45%; or from 45 to 50%; or from 50 to 55%; or from 55 to 60%; or from 60 to 65%; or from 65 to 70%; or from 70 to 75%; or from 75 to 80%; or from 80 to 85%; or from 85 to 90%; or from 90 to 95%.

In preferred embodiments, this ratio is from 5 to 90%, or from 8 to 75%, or from 10 to 50%.

The chromatography step 4 is an ion exclusion chromatography step, carried out in a suitable chromatographic unit comprising an ion exchange stationary phase, in general an ion exchange resin—but it is not used in ion exchange mode.

The principle of ion exclusion chromatography is that the stationary phase is saturated with the same ions as those contained in the inflow and that are to be reduced or removed.

In ion exclusion chromatography, the ions contained in the inflow tend to be scarcely retained by the stationary phase and to be eluted quicker than non-ionic species such as glycol.

Ion exclusion chromatography is therefore performed without net ion exchange on the stationary phase during separation.

Ion exclusion chromatography can be simply conducted by:
  injecting the inflow into the chromatographic unit;
  injecting an eluent into the chromatographic unit; and
  collecting the above-mentioned fractions at the outlet of the chromatographic unit.

The stationary phase used is advantageously a strong or weak cationic resin, or a strong or weak anionic resin.

Preferably, it is a strong cationic resin.

The resin is advantageously a copolymer of polystyrene and divinylbenzene (DVB).

According to one embodiment, the resin has a crosslinking ratio of between 2 and 12% DVB, preferably between 3 and 10%, more preferably between 4 and 9%, further preferably between 5 and 8%.

The resin may have a particle size (particle mean volume diameter Dv50) of between 100 and 800 μm for example, preferably between 200 and 350 μm.

It is advantageous to conduct the chromatographic separation step at a temperature of 10 to 160° C., preferably 40 to 100° C., and more preferably 55 to 90° C. Cooling or heating means (advantageously heating means) are provided for this purpose.

As eluent, advantageously water or an aqueous solution are used. Preferably, demineralized (and degassed) water is used.

The volume ratio of amount of eluent to amount of treated inflow is advantageously 3 or lower, preferably 2 or lower, more preferably 0.9 or lower.

Initially, the stationary phase used may be in divalent cation form for example (in particular calcium or magnesium), or more preferably in monovalent cation form (in particular potassium or most preferably sodium).

However, in use, the ionic form of the stationary phase changes to reach ionic equilibrium with the inflow. On account of the different affinity of the monovalent and multivalent ions for the stationary phase, the proportions of monovalent and multivalent ions on the stationary phase generally differ from those of the inflow.

In particular embodiments, the stationary phase therefore contains 5 to 95%, preferably 20 to 90% and more preferably 55 to 80% of multivalent ions (and more particularly divalent ions) relative to the total content, these proportions being given in molar equivalents.

This ionic form of the stationary phase can be measured by displacement of the ions fixed onto the stationary phase e.g. by injection of excess acid (such as hydrochloric acid) followed by measurement of the contents of eluted ions using ionic HPLC chromatography for example.

The chromatographic separation step may be batch-wise, semi-continuous or continuous, preferably it is semi-continuous or continuous.

The chromatographic unit may be formed of a single column. But preferably it is a multi-column unit, preferably having no more than 11 columns, or no more than 8 columns, more preferably no more than 6 columns and further preferably no more than 4 columns and ideally fewer than 4 columns.

The chromatographic unit may have a static bed or preferably a non-static bed.

A chromatographic unit with non-static bed is a multi-column system wherein the relative positions of the bed of the stationary phase and the flow injection or collection points move over time.

Examples of such chromatographic units with non-static bed are simulated moving bed (SMB), improved simulated moving bed (iSMB), sequential simulated moving bed (SSMB), actual moving bed (AMB), VARICOL™, MODICON™, POWERFEED™, MCSGP or GSSR (Gradient with Steady State Recycle) systems.

An SMB system comprises a plurality of individual columns containing an adsorbent, that are connected in series. The flow of eluent passes through the columns in a first direction. The injection points of the feed flow (flow to be treated) and of the eluent, and the collection points of the separated fractions are periodically and simultaneously moved by means of a set of valves. The overall effect is to simulate the operation of a single column containing a moving bed of solid adsorbent, the solid adsorbent moving in a counter-current direction relative to the flow of eluent. Therefore, an SMB system is composed of columns containing stationary beds of solid adsorbent through which the eluent passes, but the operation is such that a continuous counter-current moving bed is simulated.

The most conventional form of an SMB system is the four-section SMB system. Other possible forms are three-section SMB systems and two-section SMB systems (such as described in the article "Two Section Simulated Moving Bed Method" by Kwangnam Lee, in Separation Science and Technology 35(4):519-534, 2000, to which express reference is made).

In iSMB and SSMB systems, there is at least one step at which the system operates in a closed loop, without any inlet or outlet of product.

An iSMB system is such as described in documents EP 0342629 and U.S. Pat. No. 5,064,539, to which express reference is made.

An SSMB system divides the feeds and collections of flows into sub-sequences applied periodically.

Other variants of SMB systems are: the time variable SMB system and the POWERFEED™ system such as described in the document U.S. Pat. No. 5,102,553 and in the article "PowerFeed operation of simulated moving bed units: changing flow-rates during the switching interval", by Zhang et al. in Journal of Chromatography A, 1006:87-99, 2003, to which express reference is made; the MODICON™ system such as described in document U.S. Pat. No. 7,479,228 to which express reference is made; and the SMB system with internal recirculation such as described in document U.S. Pat. No. 8,282,831, to which express reference is made.

An AMB system operates in similar manner to an SMB system. However, instead of moving the injection points of the feed flow and eluent, and the collection points, using a valve system, a set of adsorption units (columns) are physically moved relative to the feed and collection points. Again, the operation makes it possible to simulate a counter-current continuous moving bed.

A VARICOL™ chromatography system is such as described in documents U.S. Pat. Nos. 6,136,198, 6,375,839 6,413,419 and 6,712,973, to which express reference is made. A VARICOL™ system comprises a plurality of individual columns containing an adsorbent and connected in series. The eluent is passed through the columns in a first direction. Contrary to the SMB system, the injection points for the flow to be separated and for the eluent, and the collection points of the fractions separated in the system, are periodically but asynchronously moved using a set of valves. The overall effect is to create separation zones having a length which varies over time, thereby dynamically allocating the stationary phase to sections where it is most useful, and allowing similar separation capacity but with fewer chromatographic separation units and increased productivity. Contrary to an SMB system, a VARICOL™ system does not simulate the functioning of a single column containing a moving bed of solid adsorbent, the solid adsorbent moving in a counter-current direction to the flow of eluent, and therefore the operating principle of the VARICOL™ system cannot be implemented in an equivalent AMB system.

Figure 2:
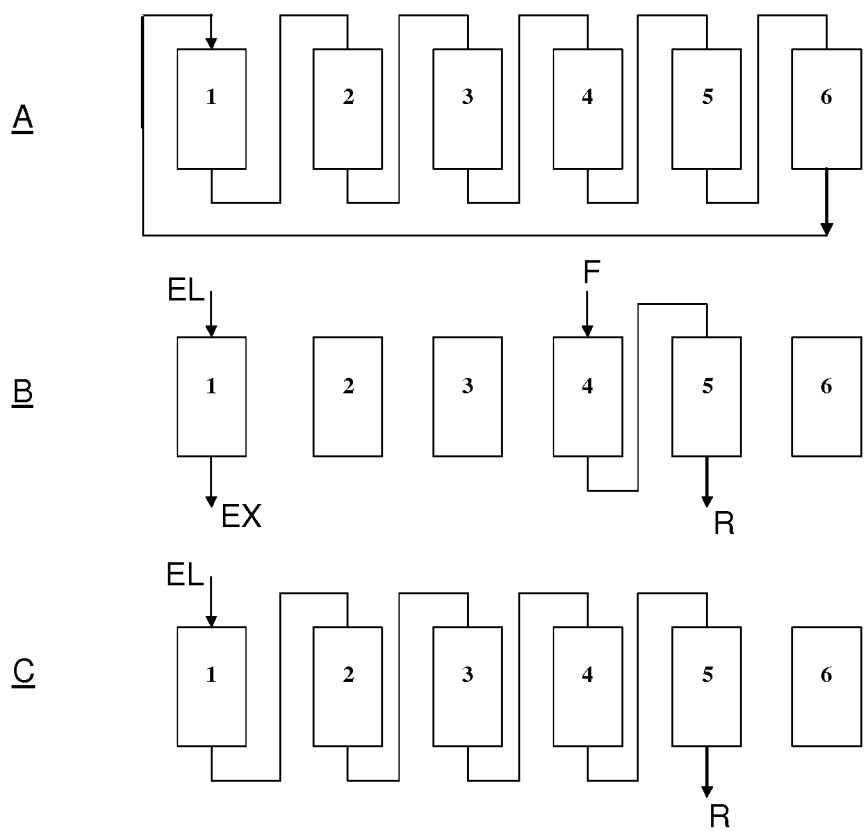
FIG. 2 schematically illustrates a chromatographic unit allowing the implementation of the method according to one embodiment of the invention

One preferred example of a simulated moving bed is illustrated in FIG. 2, in the form of a chromatography system of sequential simulated moving bed type (SSMB) on six compartments or columns. This system can be operated with four-phase cyclic functioning.

Phase No. 1 (part A in the Figure): loop phase during which continuous circulation is maintained in a closed loop on all the compartments placed in series, to move the interstitial volume from one compartment to the next without injection of eluent.

Phase No. 2 (part B in the Figure): feed/injection of feed. The flow feed (F) is injected at the head of the fourth compartment. Simultaneously, a substantially identical volume of raffinate (R) is collected at the outlet of the fifth compartment. Compartments 4 and 5 here form section 3. Compartments 2 and 3 form the separation section between the extract and injection of feed. Here they form section 2.

Phase No. 3 (part B in the Figure): eluting of the extract. The eluent (EL) is injected onto the first compartment to elute the extract (EX), which is collected in substantially identical volume at the bottom of the first compartment. Here compartment No. 1 forms section 1.

Phases No. 2 and 3 are preferably operated simultaneously to increase the productivity of the system.

Phase No. 4: elution of the raffinate. The eluent (EL) is injected at the head of the first compartment and the raffinate (R) is collected in substantially identical volume at the outlet of the fifth compartment. Here compartment No 6 is a buffer compartment ensuring separation between the tail of the extract and the head of the raffinate. It forms section 4. This section can be omitted if the desired degree of purity and/or yield is relatively limited.

These phases are operated in order in one preferred embodiment, from 1 to 4. Their succession forms a complete sequence.

Each sequence (phases No. 1 to 4) is repeated six times, offsetting the inlets and outlets of the compartments by incrementing the compartment number from left to right in the system; the feed is therefore injected at the top of compartment No. 1 in sequence No. 1, then at the top of compartment No. 2 in sequence No. 2, etc.

A complete production cycle is obtained after completion of the six successive sequences, when the feed injection point initially at the inlet to compartment No. 1, again returns to the inlet of compartment No. 1.

In the foregoing, a description was given of the SSMB system with reference to the case in which the compartments correspond to columns. This is not limiting, and the invention also applies to systems in which the compartments are parts of columns.

Also, the number of columns present in sections 1, 2, 3 and 4 may vary as a function of the desired quality of separation. It is therefore possible to envisage systems of same type with one, two, three, four compartments and up to twelve compartments or more.

The method can also be implemented in a non-continuous multi-column installation with closed or open loop, such as the DCC system described in patent WO 2007/012750.

According to one embodiment, the yield of chromatographic separation is 97% or higher, preferably 98% or higher, more preferably 99%, or higher, further preferably 99.5% or higher. This yield corresponds to the molar percentage of glycol in the inflow which is recovered in the glycol-enriched fraction.

Advantageously, the salt removal rate in chromatographic separation is 50% or higher, preferably 80% or higher, more preferably 85% or higher, further preferably 90% or higher, or even 95% or higher. This removal rate corresponds to the molar percentage of salts dissolved in the inflow that is not found in the glycol-enriched fraction.

In particular, the removal rate of the $Na^+$ cation in the chromatographic separation is preferably 50% or higher, or 80% or higher, or 85% or higher, or 90% or higher, or 92% or higher, or 94% or higher, or 95% or higher.

Similarly, the removal rate of the $K^+$ cation in the chromatographic separation is preferably 50% or higher, or 80% or higher, or 85% or higher, or 90% or higher, or 92% or higher, or 94% or higher, or 95% or higher.

Similarly, the removal rate of the $Ca^{2+}$ cation in the chromatographic separation is preferably 50% or higher, or 80% or higher, or 85% or higher, or 90% or higher, or 92% or higher, or 94% or higher, or 95% or higher.

Similarly, the removal rate of the $Mg^{2+}$ cation in the chromatographic separation is preferably 50% or higher, or 80% or higher, or 85% or higher, or 90% or higher, 92% or higher, or 94% or higher, or 95% or higher.

Similarly, the removal rate of the $Cl^-$ anion in the chromatographic separation is preferably 50% or higher, or 80% or higher, or 85% or higher, or 90% or higher, or 92% or higher, or 94% or higher, or 95% or higher.

Similarly, the removal rate of the $SO_4^{2-}$ anion in the chromatographic separation is 50% or higher, or 80% or higher, or 85% or higher, or 90% or higher, or 92% or higher, or 94% or higher, or 95% or higher.

Similarly, the removal rate of the $CO_3^{2-}$ anion in the chromatographic separation is preferably 50% or higher, or 80% or higher, or 85% or higher, or 90% or higher, or 92% or higher, or 94% or higher, or 95% or higher.

The invention advantageously avoids the need for any glycol distillation step.

Similarly, and advantageously, no other separation step of the salts or ions is performed either before or after the chromatographic separation step. In particular, advantageously no provision is made for a crystallization and crystal decanting step.

The glycol-enriched fraction is advantageously subjected to additional treatment for concentrating it, i.e. reducing its water content. Therefore, an evaporation step can be used, or a separation step using reverse osmosis.

Preferably, the excess water collected during this additional treatment is recycled as eluent for the above-described chromatographic step.

The glycol-enriched fraction recovered by means of the method of the invention (optionally after the above-mentioned additional treatment) provides a regenerated anti-hydrate agent that can be used for the extraction or conveying of hydrocarbons, to ensure the stability of the multiphase mixture extracted from the deposit against risks of gas hydrate formation.

It is to be noted that one advantage of the invention is that it requires no (or practically no) regeneration of the stationary phase, due to the operation in ion exclusion mode and not in ion exchange mode, and due to the fact that separation is not materially affected by changes in the proportion of the different ions on the resin over time. By "regeneration of the stationary phase" is meant washing of the stationary phase with a specific washing solution intended to recondition this phase to a particular ionic form capable of allowing efficient chromatographic separation.

The passing of a washing solution through the stationary phase may however, in some cases, be appropriate to clean the phase in the event of accumulation of contaminants such as precipitated species or adsorbed organic compounds.

For example, with a multi-column installation (in particular of SMB type or the like) it is possible to provide one or more cleaning zones allowing a column to be disconnected from the separation loop, for periodic or occasional desorbing of contaminants, and optionally to re-equilibrate the stationary phase with the inflow.

According to one embodiment, the stationary phase undergoes washing less than once a week, or less than once every two weeks, or less than once a month, or less than once a quarter, or less than once a half-year, or less than once a year.

According to one embodiment, at least 20 kg of glycol, preferably at least 40 kg of glycol, more preferably at least 90 kg of glycol, further preferably at least 260 kg of glycol, still further preferably at least 950 kg of glycol per liter of stationary phase passes through the chromatographic unit before the stationary phase is subjected to washing. Ideally, the stationary phase does not undergo any washing i.e. it is solely subjected to injection of the inflow and eluent.

EXAMPLES

The following examples give non-limiting illustrations of the invention.

Example 1

In this example, three different "pulses" (feeds of solutions to be separated having a small volume) are injected under identical conditions into a chromatographic unit operating in ion exclusion mode. These three experiments make it possible to compare the separation of salts from MEG, DEG and TEG respectively.

The compositions of the three solutions used for the three pulses were as follows:
  850 g/L of MEG+13.2 g/L of NaCl+15.5 g/L of $CaCl_2$, i.e. a ratio (divalent cations/total cations) expressed in equivalents of 55%.

850 g/L of DEG+13.2 g/L of NaCl+15.5 g/L of CaCl$_2$ i.e. a ratio (divalent cations/total cations) expressed in equivalents of 55%.

850 g/L of TEG+13.2 g/L de NaCl+15.5 g/L of CaCl$_2$ i.e. a ratio (divalent cations/total cations) expressed in equivalents of 55%.

Each pulse represents a volume of solution equal to 1% of the resin volume (0.01 BV).

Each pulse was injected at the top of a double-wall chromatographic column containing a strong cationic resin in about 60% divalent form (i.e. about 40% monovalent form), after prior equilibrating with a mixture of industrial origin containing 34% divalent cations (relative to the total amount of cations, in equivalents). The column measured 2.5 cm in diameter, the resin height was 90 cm, and the resin volume was 440 mL; the temperature was set at 65° C.

Eluting was performed with demineralized water at a temperature of 65° C. and a flow rate of 20 mL/min. The liquid leaving the column was collected and fractionated using a sampler to analyze the conductivity and dry matter content (in Degrees Brix) of each of the fractions collected. When all the injected feed had been eluted and the column rinsed, a new pulse was injected: the three experiments were therefore conducted in series.

The conductivity value of each sample represented the salt concentration in the sample.

The dry matter content in Degrees Brix (or grams of dry matter per 100 g of solution) was obtained by measuring the refractive index in diluted solutions (since the dry matter content is proportional to the refractive index).

The resin used was Applexion® XA EG 1.

Figure 3:
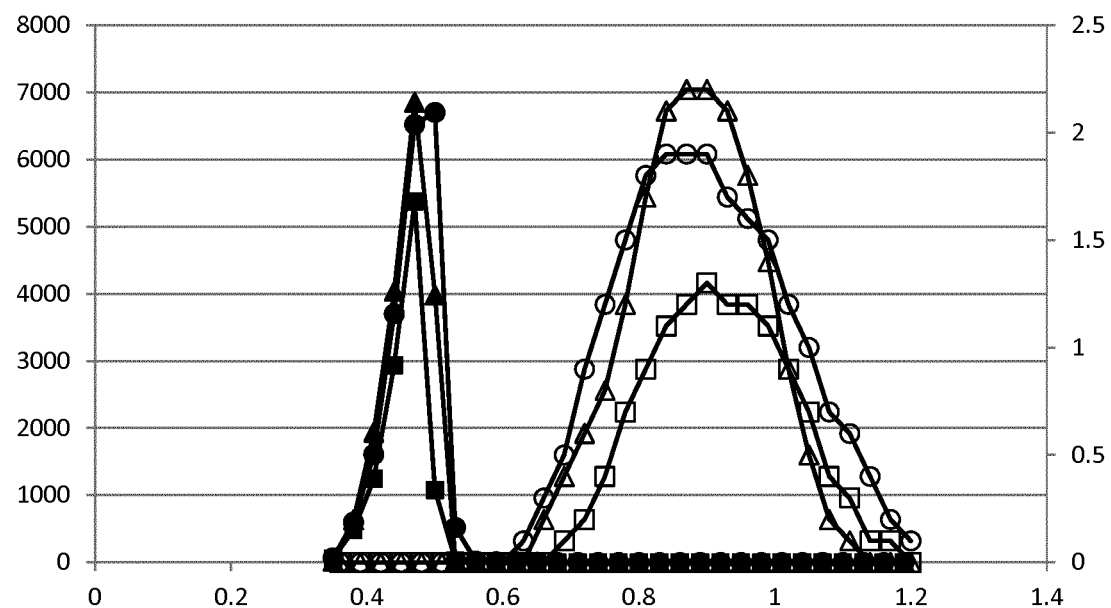
FIG. 3 is a graph illustrating the chromatograms obtained in Example 1, by injection of three solutions of MEG, DEG and TEG respectively containing the same concentrations in glycols and salts. The volume of injected eluent (in BV units, meaning resin volume) is shown along the X-axis. The conductivity of the fraction concerned is shown in $\mu S/cm$ on the left side of the Y-axis, and the content of dry matter in % Brix is shown on the right side of the Y-axis. The curve with the triangle symbols is the one obtained with the MEG solution; the curve with the square symbols is the one obtained with the DEG solution; and the curve with the circular symbols is the one obtained with the TEG solution. Black-colored symbols correspond to the conductivity measurement, and non-colored symbols correspond to the dry matter content measurement.

The results obtained are provided in FIG. 3.

It can be seen that the salts and glycols were very efficiently separated, with return to baseline between the salt peak and glycol peak. In addition, the retention time of each glycol was the same even though the molar masses of the three glycols are different (retention volumes of 0.88 BV for MEG, 0.92 BV for DEG and 0.90 BV for TEG, i.e. an average of 0.90 BV).

Similarly, the retention time of the salts did not vary from one pulse to another (near-constant retention volume at 0.47 BV).

The separation performance was therefore substantially identical for MEG, DEG and TEG.

Example 2

The methodology in Example 1 was repeated to examine the separation of a pulse of a rich glycol industrial solution from an offshore platform.

This solution was composed of 840 g/L MEG and 29 g/L salts, with a ratio in equivalents (divalent cations/total cations) of 34%. The flow rate, temperature and injected volume conditions were the same as previously.

The chromatographic column was filled with strong cationic resin conditioned in three different forms:
100% potassium;
100% calcium;
60% divalent (majority Ca)/40% monovalent (majority Na), i.e. an equilibrated form obtained after saturation of the resin with the industrial solution.

The resin used was Applexion® XA EG 1.

Figure 4:
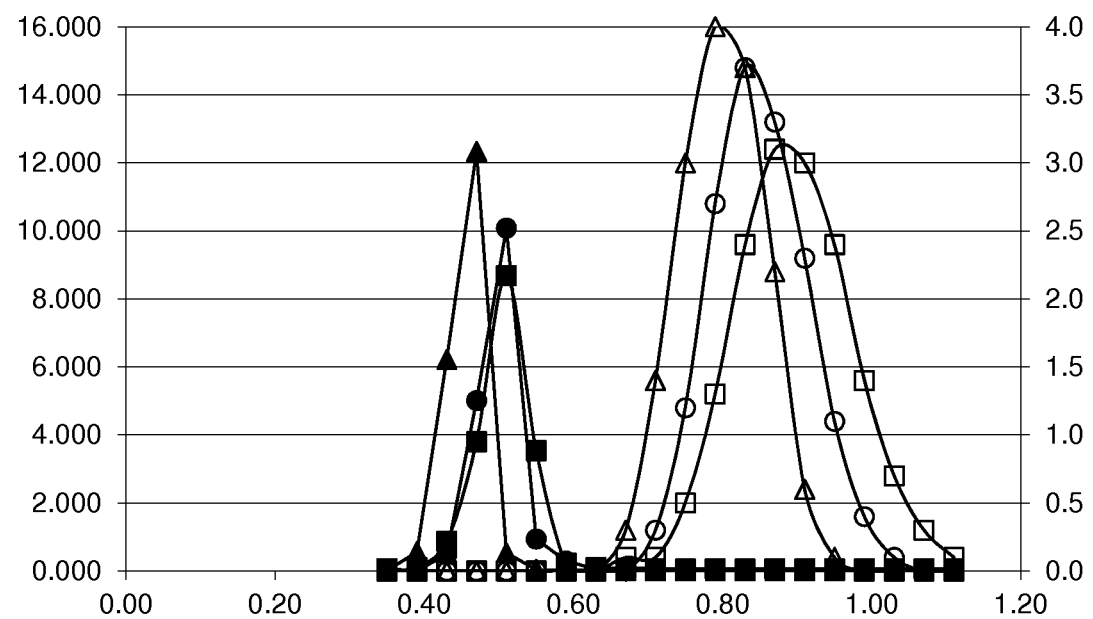
FIG. 4 is a graph illustrating the chromatograms obtained in Example 2, by injection of an industrial rich MEG solution on a cationic resin in three different ionic forms: K, Ca, and 65% Ca-35% K. The volume of injected eluent (in BV units) is provided on the X-axis. The conductivity of the fraction concerned is shown in mS/cm on the left side of the Y-axis, and the content of dry matter in % Brix is shown on the right side of the Y-axis. The curve with the triangle symbols is the one obtained with the resin in K form; the curve with square symbols is the one obtained with the resin in Ca form; and the curve with the circular symbols is the one obtained with the resin in 65% Ca-35% K form. Black-colored symbols correspond to the conductivity measurement, and non-colored symbols correspond to the dry matter content measurement.

The results are provided in FIG. 4.

These results show:
a complete separation between the salt peak and MEG peak irrespective of the ionic form of the resin;

an increase of only 10 to 15% in retention times both for salt and for MEG between the extreme forms of the resin i.e. the K form and Ca form. In practice, the resin changes between its initial form (typically K) and a form in which the K and Ca ions are in equilibrium on the resin, and therefore the variations in retention times are correspondingly low.

This example demonstrates that the efficacy of exclusion of ions in solution, and hence the separation of glycol from sodium, potassium, calcium and magnesium salts in solution, is not a function of the ionic form of the strong cationic resin provided that the phases are in equilibrium (ion exchanges between monovalent and divalent ions of the resin if the monovalent/divalent ratio of the mixture to be separated varies throughout injections).

Example 3

In this example, the purpose was to study a profile of excess product load in the resin performed on the chromatography column, using a product with very high salt content.

The treated mixture used comprised 225 g/L MEG and 247 g/L salts, with a divalent cations/total cations ratio of 34%, identical to the ratio used in the preceding examples.

Excess loading was obtained by saturating the resin with a large volume of representative industrial product to examine the thermodynamic and competitive effects of the different compounds.

A volume of 1.5 BV of mixture was thus percolated through the column at 65° C., at a flow rate of 20 mL/min; the outgoing liquid was collected and fractionated into about twenty instant samples. After passing this volume of mixture, the column was rinsed with 2 BV of demineralized water. During the rinsing phase, samples were taken in the same manner as for the product saturation phase.

The collected samples were analyzed to measure the concentrations of MEG, Na, Ca, Cl, K and Mg.

The resin used was Applexion® XA EG 2.

Figure 5:
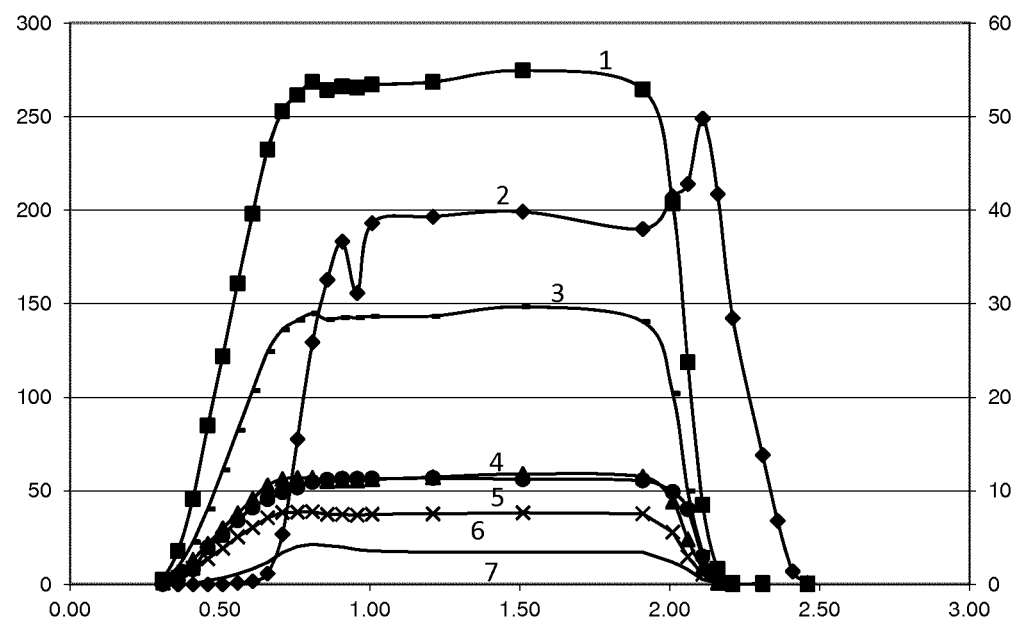
FIG. 5 is a graph illustrating the chromatograms obtained in Example 3, using an excess with an industrial solution of rich MEG having a salt concentration higher than its MEG concentration, on a strong cationic resin resistant against variations in osmotic pressure and previously ionically equilibrated with this product, then rinsed with demineralized water. The injected volume (in BV units) is provided on the X-axis. The concentration of each species in g/L is shown on the Y-axis. The scale on the right is used for the potassium and magnesium ions, and the scale on the left is used for the other species. Curve 1 corresponds to the total salt concentration, curve 2 corresponds to MEG concentration, curve 3 corresponds to Cl⁻ concentration, curve 4 corresponds to Na⁺ concentration, curve 5 corresponds to $Ca^{2+}$ concentration, curve 6 corresponds to $K^+$ concentration and curve 7 corresponds to $Mg^{2+}$ concentration

The results obtained are provided in FIG. 5.

The profiles of the ionic species show that the different mineral salts contained in the treated mixture have the same affinity for the resin: they leave the column at the same time and are also rinsed at the same time. As for the pulses in the preceding examples, it can be seen that the salts are the first to leave the resin and that MEG leaves about 0.3 BV later.

This separation between the species, with adsorption and desorption on a resin equilibrated with the mixture to be treated, demonstrates the robustness of the invention which is noteworthy having regard to the strong salt concentration applied of 250 g/L.

Example 4

In this example, the purpose was to study the MEG and salt matter profile in a continuous chromatographic system of SSMB type having 6 columns, of the type illustrated in FIG. 2 and operated at a temperature of 60° C.

The resin used was Applexion® XA EG 1.

The mixture to be separated was the same as in Example 2. It was injected discontinuously between the extract and raffinate collection points. The MEG retained by the resin concentrated in the extract whilst the salts, that were excluded, were eluted in opposite direction towards the raffinate zone. The two fractions, extract and raffinate, were semi-continuously drawn off from the system in similar manner to the injection of water and mixture to be separated.

Figure 6:
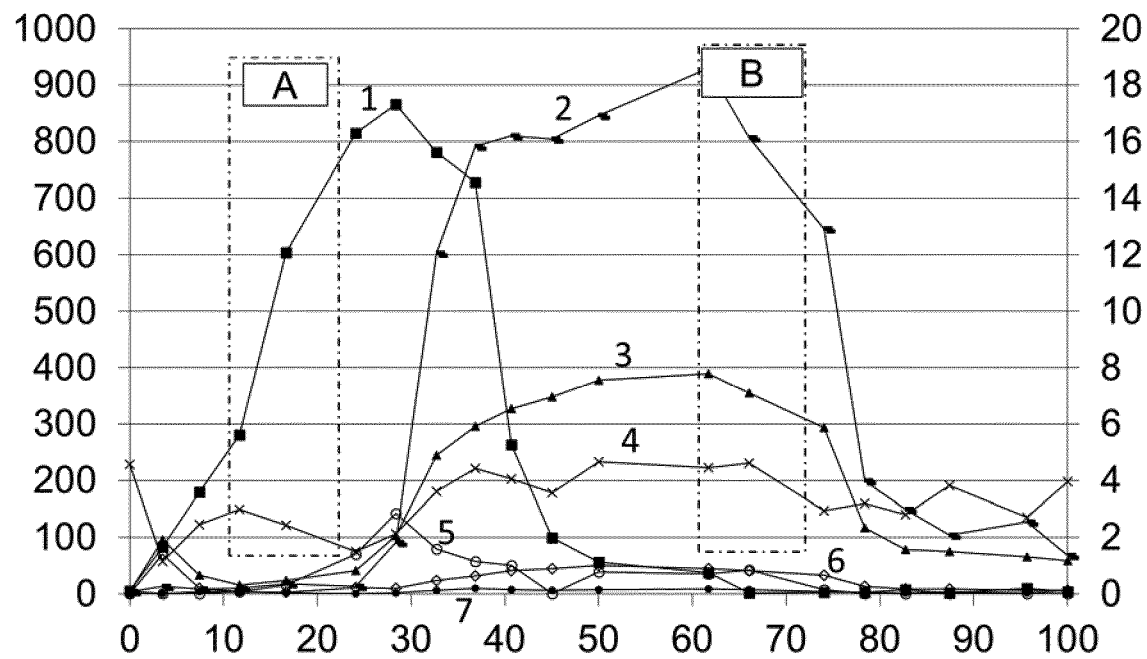
FIG. 6 is a graph illustrating the chromatograms obtained in Example 4, with separation in a continuous chromatographic system of SSMB type. The cycle time percentage is provided on the X-axis. The concentration in different species in g/L is shown on the Y-axis. The scale on the right is used for all the salts, and the scale on the left is used for MEG. Curve 1 corresponds to MEG concentration, curve 2 corresponds to Cl⁻ concentration, curve 3 corresponds to Na⁺ concentration, curve 4 corresponds to $Ca^{2+}$ concentration, curve 5 corresponds to acetate concentration, curve 6 corresponds to $K^+$ concentration and curve 7 corresponds to $Mg^{2+}$ concentration. The part of the graph labelled A corresponds to the extract, and the part labelled B corresponds to the raffinate.

The results are shown in FIG. 6.

This profile corresponds to a MEG recovery rate of 99.8% in the extract fraction (amount of MEG recovered in the extract relative to the total amount injected into the system), and a salt removal rate of 95.5% in the raffinate fraction (amount of removed salts in the raffinate relative to the total amount of salts injected into the system).

The invention claimed is:

1. A purification method comprising:
   a) providing a flow comprising a glycol, monovalent ions and divalent cations wherein the monovalent ions comprise $Na^+$ and optionally $K^+$ cations, and the divalent cations comprise $Ca^{2+}$ and optionally $Mg^{2+}$ cations and wherein the flow has a ratio, in equivalents, of divalent cations to total cations of 5 to 90%; and
   b) treating this flow with ion exclusion chromatography comprising:
      i) injecting the flow into an ion exclusion chromatographic unit comprising an ion exchange stationary phase, wherein the stationary phase is a strong cationic resin partly in monovalent cationic form and partly in divalent cationic form;
      ii) injecting an eluent into the ion exclusion chromatographic unit, wherein the eluent is water; and
      iii) collecting a fraction at the outlet of the ion exclusion chromatographic unit;
      the collected fraction being enriched with glycol and depleted of monovalent ions and divalent cations relative to the flow,
   wherein the ion exclusion chromatography leads to separation of glycol both from monovalent ions and from divalent cations.

2. The method according to claim 1, comprising a subsequent step of concentrating the collected fraction.

3. The method according to claim 1, wherein the glycol is selected from monoethylene glycol, diethylene glycol, triethylene glycol and mixtures thereof.

4. The method according to claim 1, wherein the monovalent ions comprise $Na^+$ and $K^+$ cations, and the divalent cations comprise $Ca^{2+}$ and $Mg^{2+}$ cations.

5. The method according to claim 4, wherein the flow has a ratio, in equivalents, of divalent cations to total cations of 8 to 90%.

6. The method according to claim 1, wherein the chromatographic unit is a multi-column unit with non-static bed.

7. The method according to claim 1, wherein the treatment of the flow by ion exclusion chromatography is conducted at a temperature of 10 to 160° C.

8. The method according to claim 1, wherein in the collected fraction at least 50 mol. % of the monovalent ions and divalent cations contained in the flow are removed.

9. The method according to claim 1, wherein at least 20 kg of glycol per liter of stationary phase passes through the chromatographic unit before the stationary phase is subjected to washing.

10. A method to regenerate an anti-hydrate agent, comprising:
    a) providing a multiphase mixture comprising hydrocarbons, a glycol and dissolved salts;
    b) separating the hydrocarbons from this mixture, so as to recover an aqueous phase; and
    c) applying the purification method of claim 1 to the aqueous phase as a flow, and recovering a regenerated composition of anti-hydrate agent in the form of the collected fraction.

11. The method according to claim 10, comprising a step of clarifying the aqueous phase before applying the purification method.

* * * * *